United States Patent [19]

Newman

[11] Patent Number: 4,546,859

[45] Date of Patent: Oct. 15, 1985

[54] ADJUSTABLE STOP FOR DISPENSING SYRINGE

[75] Inventor: Howard F. Newman, Los Angeles, Calif.

[73] Assignee: American Hospital Supply Corporation, Evanston, Ill.

[21] Appl. No.: 205,117

[22] Filed: Nov. 10, 1980

Related U.S. Application Data

[60] Continuation of Ser. No. 17,662, Mar. 5, 1979, abandoned, which is a division of Ser. No. 836,995, Sep. 27, 1977, Pat. No. 4,173,225.

[51] Int. Cl.$^4$ .................. B65H 59/10; B23B 45/14; B23B 49/00
[52] U.S. Cl. .................................. 188/67; 222/43; 408/241 S; 604/209
[58] Field of Search .............. 188/65.1, 67; 92/23; 74/531, 162; 128/218 C, 218 F; 192/138, 143; 408/192, 202, 241 S; 83/468; 73/429; 141/26, 27; 222/43, 47, 309; 604/187, 209, 117, 129, 186, 157, 151

[56] References Cited

U.S. PATENT DOCUMENTS

| | | | |
|---|---|---|---|
| 717,296 | 12/1902 | Spalding | 188/67 |
| 2,180,209 | 11/1939 | Johnson | 74/531 |
| 2,632,445 | 3/1953 | Kas | 188/67 |
| 2,833,168 | 5/1958 | Nelson | 408/202 |
| 2,863,452 | 12/1958 | Ogle | 128/218 C |
| 3,554,094 | 1/1971 | Gross | 188/67 |
| 3,783,876 | 1/1974 | Dye | 128/347 |
| 3,831,602 | 8/1974 | Broadwin | 128/218 C |
| 3,965,945 | 6/1976 | Ross | 128/218 C |
| 4,003,499 | 1/1977 | Shapiro et al. | 222/309 |
| 4,026,288 | 5/1977 | Costa et al. | 128/218 F |
| 4,098,276 | 7/1978 | Bloom et al. | 128/218 C |
| 4,113,404 | 9/1978 | Lippacher et al. | 408/202 |
| 4,159,784 | 7/1979 | d'Autry | 222/47 |

FOREIGN PATENT DOCUMENTS

| | | | |
|---|---|---|---|
| 2362638 | 3/1978 | France | 128/218 C |
| 668710 | 3/1952 | United Kingdom | 188/72.7 |

Primary Examiner—Douglas C. Butler
Attorney, Agent, or Firm—Roger A. Williams

[57] ABSTRACT

An adjustable stop for gripping a rod at selected locations intermittent the length of the rod, including a base member with a pair of longitudinally spaced openings for receiving a rod having a longitudinal axis. A clamp member is provided with an opening located between the base member openings for receiving the same rod. A cam surface is provided on the clamp member for engaging the base member to misalign the clamp member opening between the two base member openings for gripping the rod with the three openings as the clamp member is rotated about the rod's longitudinal axis when the rod extends through the adjustable stop. A pair of laterally spaced abutment portions are provided on the base member, which abutment portions are separated by a distance substantially greater than the rod's transverse dimension for slidingly engaging only a portion of the periphery of a supporting structure that is substantially larger than the rod so that remaining portions of the supporting structure remain free for performing other functions as the stop moves relative to the supporting structure in a direction generally parallel to the rod's longitudinal axis as the abutment portions limit rotational movement of the stop during longitudinal adjustment.

6 Claims, 4 Drawing Figures

ADJUSTABLE STOP FOR DISPENSING SYRINGE

This application is a continuation, of application Ser. No. 017,662, filed Mar. 5, 1979, now abandoned, which is a division of application Ser. No. 836,995, filed Sept. 27, 1977, now U.S. Pat. No. 4,173,225.

BACKGROUND OF THE INVENTION

A dispensing syringe with an adjustable dose setting mechanism is described in a co-pending application entitled Syringe Pumping Handle Grip and Method of Assembling Same, of Bloom et al, Ser. No. 747,417, filed Dec. 6, 1976, now U.S. Pat. No. 4,098,276. That application describes a coil spring stop that is adjustably mounted on a rod-like dose control rod.

It has been found that under long continuous use the coil spring stop of the above application is sufficiently easy to manually adjust, but does tend to creep from its initial setting with long continued use of the dispensing syringe. Thus, it may be necessary to periodically re-check the setting and correct any deviation slippage of the stop on its supporting rod.

SUMMARY OF THE INVENTION

This invention is an improvement on a stop mechanism for a dispensing syringe that is very easy to adjust, but still gives very tight noncreeping gripping attachment to a rod-like member of the dispensing syringe. The stop includes a pair of members with openings that receive the rod-like member, and a cam on one of the members engages the other member to cause the holes to misalign and thereby firmly gripping the rod-like member. A form of the invention is shown that includes a U-shaped base with a pair of arms having openings through which the rod-like member extends. A clamping member with an opening for the rod fits between the arms of the base and has a cam structure for misaligning openings in the base and clamping structure. Preferably the base has a recess for slidingly receiving a portion of a cylindrical syringe barrel to keep the base from rotating on the rod-like member during adjustment.

THE DRAWINGS

DETAILED DESCRIPTION

Figure 1:
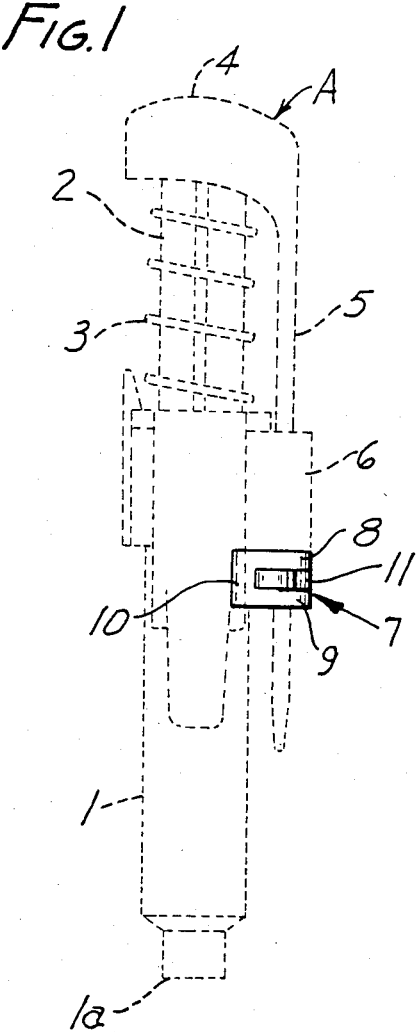
FIG. 1 is a side elevational view of a dispensing syringe with the adjustable stop abutting a portion of the syringe.

In FIG. 1 a syringe barrel 1 is shown with a longitudinally slidable plunger 2 that is urged toward a fully retracted position by compression coil spring 3. Limiting the position of the retracted plunger 2 is a dose control device A that includes a cap 4 fitting over the plunger 2 and a metering rod 5. Metering rod 5 is longitudinally slidable within an opening in a handle portion 6 that fits on syringe barrel 1. The details of the syringe handle 6, and metering rod 5 are shown in the co-pending application by Bloom et al previously mentioned. It is well understood that a forward tip of 1a the syringe barrel 1 can connect to a dispensing tube, needle, etc.

Fitting on metering rod 5 is a cam locking stop mechanism that includes a U-shaped base 7 with a pair of arms 8 and 9. Arms 8 and 9 have aligned openings through which metering rod 5 extends. The U-shaped member also has a floor section 10 which can slide along the syringe barrel 1 as the metering rod moves longitudinally relative to the barrel 1 during loading and dispensing a measured dose from the syringe barrel 1. To control the amount of the dose, arm 8 of the U-shaped base abuts a portion 6 of a handle structure on the syringe. To keep the U-shaped base member 7 from sliding on metering rod 5 at it continually bangs into a portion of the syringe handle, a clamping member 11 with a cam surface tightly grips the adjustable stop to the metering rod 5.

Figure 2:
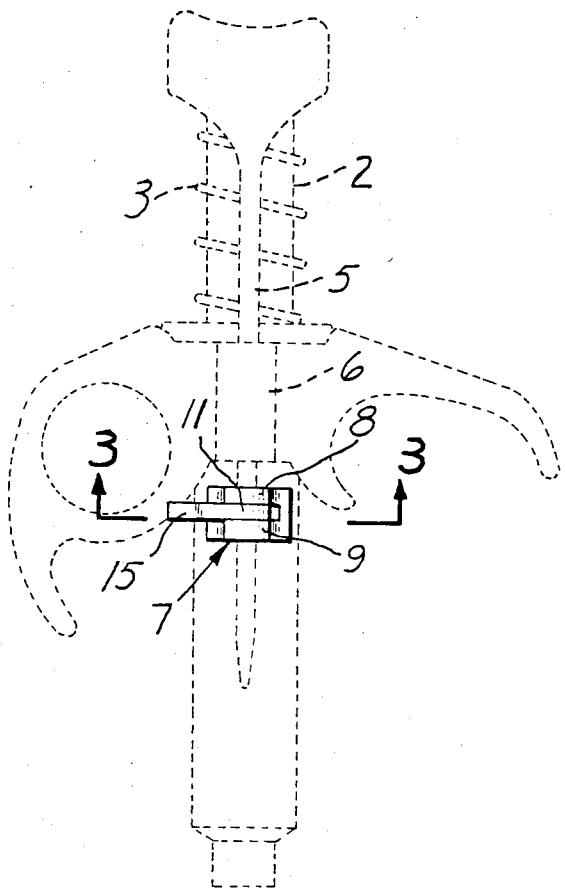
FIG. 2 is a front elevational view of the syringe of FIG. 1, but with the syringe plunger slightly depressed and the adjustable stop moved from the abutting configuration of FIG. 1.

In FIG. 2 the adjustable stop is shown in a position traveling along with metering rod 5 as plunger 2 begins its forward, shown as downward in FIG. 2, dispensing stroke. After totally dispensing the measured dose, the plunger 2 is released and the compression coil spring retracts the plunger until the adjustable stop abuts portion 6 of the syringe handle. Because of the locking structure, the adjustable stop does not creep along metering rod 5 with continual usage.

Figure 3:
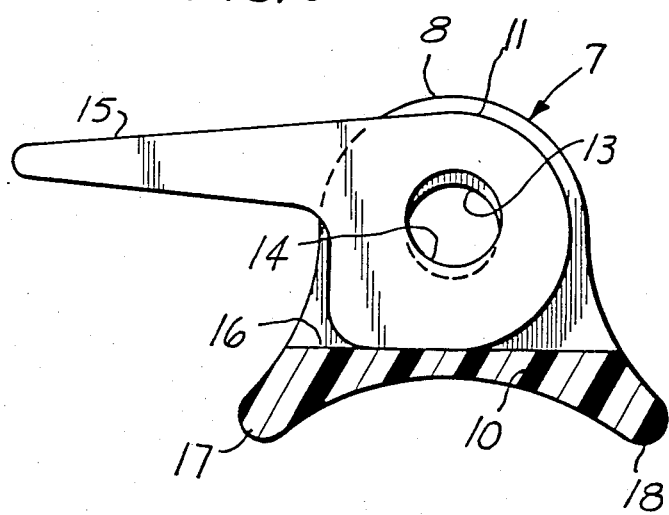
FIG. 3 is an enlarged sectional view taken along line 3—3 of FIG. 2 showing the adjustable stop in clamped position.

In the enlarged view of FIG. 3, arm 8 of the U-shaped base member has been an opening 13. The clamping member 11 has an opening 14. As a protruding handle 15 moves a camming surface 16 of clamping member 11 into contact with a floor section 10 of the base member, openings 13 and 14 are misaligned. This causes a very tight gripping force firmly positioning the stop on the metering rod 5. Metering rod 5 extends through openings 13 and 14, although such metering rod is not shown in FIG. 3 for purposes of clarity.

Figure 4:
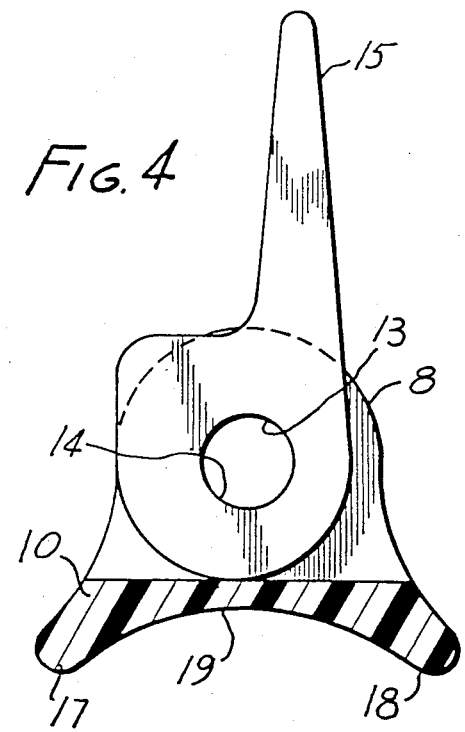
FIG. 4 is an enlarged sectional view similar to FIG. 3, but showing the adjustable stop in unclamped position.

FIG. 4 shows the clamping member moved to a position where openings 13 and 14 are properly aligned and loosely receive the metering rod 5 (not shown in FIG. 4). Thus, when the stop is as shown in FIG. 4, the stop can be manually adjusted to the desired location on metering rod 5.

Preferably the U-shaped base has a pair of protruding ears 17 and 18 with a concave recess 19 therebetween. Recess 19 can receive a portion of the cylindrical syringe barrel and protruding ears 17 and 18 can engage the syringe barrel and limit rotational movement of the base of the stop about metering rod 5. Because the surface of recess 19 is slightly spaced from the syringe barrel, it is free to longitudinally slide along the barrel without excessive frictional contact with the barrel. By preventing rotational movement of the base relative to the metering rod 5, the syringe barrel and handle can be grasped in one hand, and protruding handle 15 in another hand for easy adjustment. There is no need to hold the U-shaped base member 7 from rotating on metering rod 5.

In the foregoing description, a specific example has been used to describe the invention. However, it is understood by those skilled in the art that modifications can be made to this example without departing from the spirit and scope of the invention.

I claim:

1. An adjustable stop for gripping a rod at selected locations intermittent the length of the rod, comprising: a base member with a pair of longitudinally spaced openings for receiving a rod with a longitudinal axis; a clamp member with an opening located between the base member openings for receiving the same rod; a cam surface on the clamp member for engaging the base member to misalign the clamp member opening between the two base member openings for gripping such rod with the three openings as the clamp member is rotated about the rod's longitudinal axis when the rod extends through the adjustable stop; and a pair of laterally spaced abutment portions on the base member, said abutment portions being separated by a distance substantially greater than the rod's transverse dimension for slidingly engaging only a portion of the periphery of a supporting structure that is substantially larger than the rod so that remaining portions of the supporting structure remain free for performing other functions as the stop moves relative to the supporting structure in a direction generally parallel to the rod's longitudinal axis as the abutment portions limit rotational movement of the stop during longitudinal adjustment.

2. An adjustable stop as set forth in claim 1, wherein the supporting structure is generally cylindrical and the abutment portions include a pair of protruding ears with a recess therebetween for slidingly receiving the generally cylindrical supporting structure.

3. An adjustable stop as set forth in claim 1, wherein the base member is U-shaped having arms with the longitudinal spaced openings for receiving the rod, and a floor section joining the arms.

4. An adjustable stop as set forth in claim 3, wherein the cam surface of the clamp member engages the floor section of the U-shaped base.

5. An adjustable stop as set forth in claim 1, wherein the clamp member has a protruding handle.

6. An adjustable stop as set forth in claim 1, wherein the abutment portions include a pair of protruding ears on the base member and the base member has a recess between these ears for slidingly receiving said supporting structure.

* * * * *

UNITED STATES PATENT AND TRADEMARK OFFICE
CERTIFICATE OF CORRECTION

PATENT NO. : 4,546,859
DATED : October 15, 1985
INVENTOR(S) : Howard F. Newman

It is certified that error appears in the above-identified patent and that said Letters Patent is hereby corrected as shown below:

Column 2, line 1, "of 1a" should read -- 1a of --.

Column 2, line 24, after "Because of the" insert -- cam --.

Column 2, line 28, after "has" delete -- been --.

Signed and Sealed this

Twenty-first Day of January 1986

[SEAL]

Attest:

DONALD J. QUIGG

Attesting Officer

Commissioner of Patents and Trademarks